Figure 1:
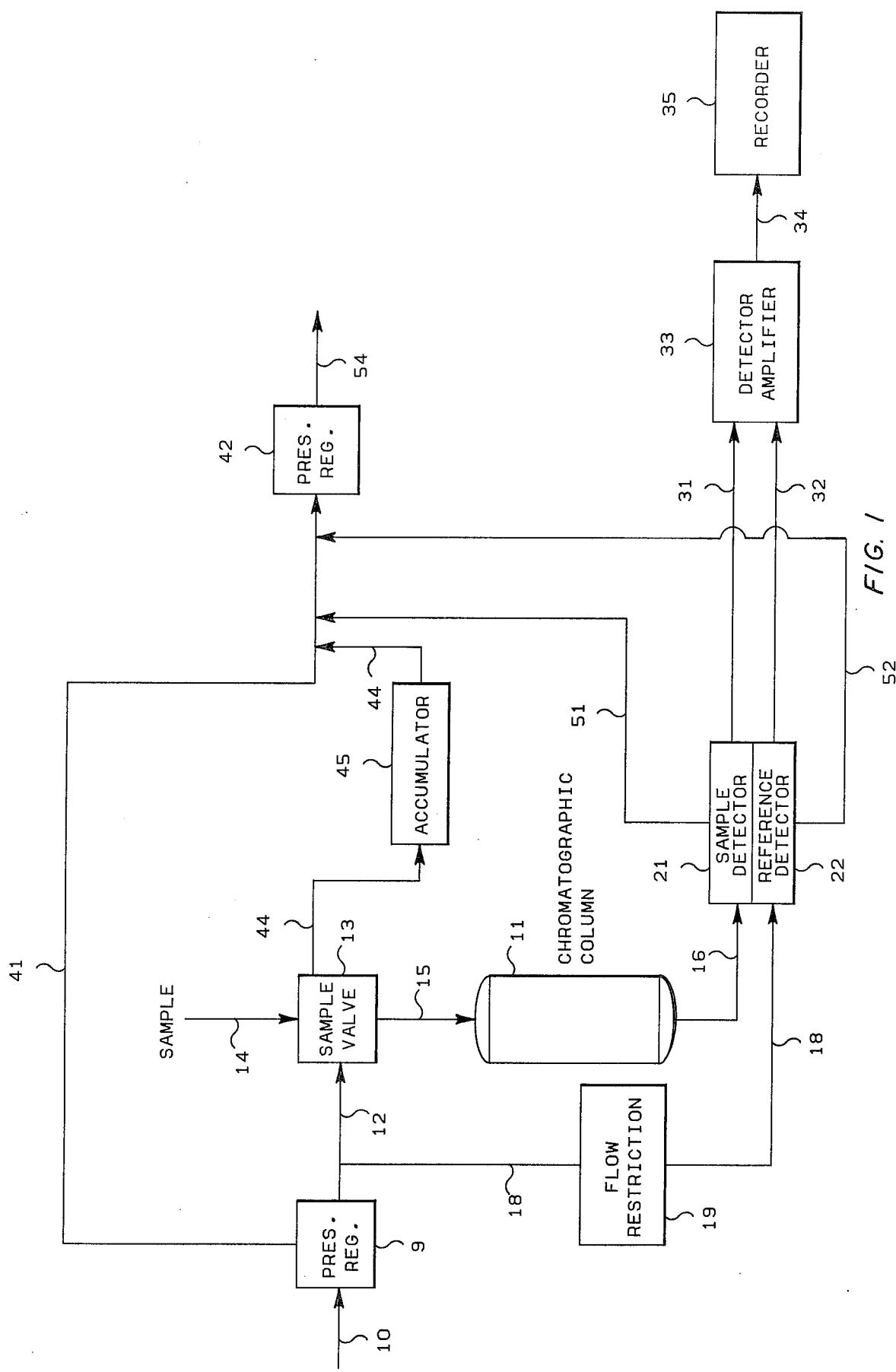

United States Patent [19]

Clardy et al.

[11] 4,196,612
[45] Apr. 8, 1980

[54] PRESSURE REGULATOR FOR A CHROMATOGRAPH

[75] Inventors: Edwin K. Clardy; Buell O. Ayers, both of Bartlesville, Okla.

[73] Assignee: Phillips Petroleum Company, Bartlesville, Okla.

[21] Appl. No.: 942,011

[22] Filed: Sep. 13, 1978

[51] Int. Cl.² ........................................... G01N 31/08
[52] U.S. Cl. ................................................ 73/23.1
[58] Field of Search ........................ 73/23.1; 422/89; 23/232 C

[56] References Cited

U.S. PATENT DOCUMENTS

| 3,240,052 | 3/1966 | Reinecke et al. | 73/23.1 |
| 3,283,563 | 11/1966 | Turner et al. | 73/23.1 |
| 4,141,237 | 2/1979 | DeFord et al. | 73/23.1 |

*Primary Examiner*—Stephen A. Kreitman

[57] ABSTRACT

A method and apparatus is disclosed for providing a very reproducible chromatographic analyzer output by reducing variations in the chromatographic analyzer output due to changes in barometric pressure. An absolute back pressure regulator is utilized to provide a reference pressure for the chromatographic analyzer system. The reference pressure is not affected by changes in barometric pressure and thus the chromatographic output is not affected by changes in barometric pressure.

Method and apparatus is also disclosed for reducing noise in a chromatographic analyzer system caused by pressure variations due to the switching of the chromatographic analyzer sample valve. A pneumatic accumulator is utilized to smooth small pressure surges resulting from actuation of the chromatographic analyzer sample valve and thus provides a smoother and more reproducible chromatographic analyzer output signal.

4 Claims, 1 Drawing Figure

PRESSURE REGULATOR FOR A CHROMATOGRAPH

This invention relates to chromatography. In a particular aspect this invention relates to method and apparatus for providing a reproducible chromatographic analyzer output signal by reducing errors caused by barometric pressure variations. In a second particular aspect this invention relates to method and apparatus for reducing the pressure variations in the chromatographic analyzer system caused by actuation of the chromatographic analyzer sample valve.

Chromatography is a known method for analyzing fluid samples by preferential absorption and desorption. In a conventional system for chromatography, a column containing appropriate adsorber, usually in granular form, is used to separate the various components of a fluid sample. The fluid can be either a gas or a liquid although the analysis is usually conducted on the sample in the gaseous state. The gas sample is introduced to the column as a slug of sample gas in a stream of carrier gas passing continuously through the column. Under the conditions of the analysis the various components of the sample are selectively adsorbed and then selectively desorbed by the continuing stream of carrier gas so that the various components of the sample pass out of the column sequentially where their presence and relative concentration can be detected by appropriate sensing means. Various means for sensing the components of a sample according to their characteristic properties include analyzers adapted to detect and record such properties as thermal conductivity, density, refractive index, infrared absorption, and the like.

The desirability of using chromatography for such specific uses as fractionator (multistage distillation) control has been recognized for some time. Certain features of process chromatography, such as specific measurement, high sensitivity, speed of analysis and simplicity of operation, make this type of analyzer very attractive for use in automatic process control.

Applications for a chromatographic analyzer in automatic process control may require a very reproducible chromatographic analyzer output over a period of time. In the past, changes in barometric pressure have often affected the reproducibility of the chromatographic analyzer output simply by changing the pressure on the gaseous streams in the chromatographic analyzer system. Such pressure changes have a direct effect on the chromatographic analyzer detector output.

Accordingly, it is a first object of this invention to provide method and apparatus for providing a reproducible chromatographic analyzer output signal by reducing errors caused by barometric pressure variations.

A thermal conductivity cell is often employed as the means for sensing the presence and concentration of the components of the sample subject to analysis. One advantage of the thermal conductivity cell as a sensing means for detecting the components of a sample is that it is linearly sensitive to the components to about 100 percent whereas other conventional detectors are linearly sensitive to about 10 percent. This allows the detector to measure the part per million peak and the approximately 100 percent peak in a binary mixture. This assumes, however, the absence or near absence of noise generated in the system. Measuring extremely small concentrations of a sample component with a chromatographic analyzer often results in a signal-to-noise ratio which is too low to make amplification of the signal effective. Sources to which the generation of noise can be attributed include temperature changes in the system and changes in the pressure and flow rates of the gaseous streams in the system. Other sources of noise are attributed to power supply, basic thermistor noise and noise caused by pressure variations caused by the actuation of the chromatographic analyzer sample valve. This invention is concerned, in part, with the reduction or control of noise caused by pressure variations arising from actuations of the chromatographic analyzer sample valve.

Accordingly, it is a second object of this invention to provide method and apparatus for reducing pressure variations in a chromatographic analyzer system caused by actuation of the chromatographic analyzer sample valve.

In accordance with the present invention method and apparatus is provided whereby an absolute back pressure regulator is utilized to provide a constant reference pressure for a chromatographic analyzer system. This is accomplished by supplying all of the gaseous streams of the chromatographic analyzer system which are normally vented to the atmosphere to the input side of the absolute back pressure regulator. These gaseous streams include the sample vent for the chromatographic analyzer sample valve, the sample vent for the chromatographic analyzer sample detector, and the carrier vent for the chromatographic analyzer reference detector. The carrier gas pressure regulator is also referenced to the constant pressure supplied by the absolute back pressure regulator instead of to atmospheric pressure. In this manner, a chromatographic analyzer system is provided whereby the pressure on the gaseous streams in the chromatographic analyzer system is a function of the carrier gas pressure and the constant pressure supplied by the absolute back pressure regulator. The pressure on the gaseous streams in the chromatographic analyzer system is not a function of atmospheric pressure; thus, variations in barometric pressure over a period of time will not affect the reproducibility of the chromatographic analyzer output.

A pneumatic accumulator is also provided in the sample vent from the sample valve to reduce noise caused by pressure variations due to the actuations of the chromatographic analyzer sample valve. A pot or piece of conduit having a larger diameter than the conduit utilized as the sample vent from the sample valve can be utilized as the pneumatic accumulator. The larger diameter of the conduit utilized as the pneumatic accumulator acts to smooth small pressure surges resulting from the actuation of the chromatographic analyzer sample valve and thus provides a smoother and more reproducible chromatographic analyzer output.

Other objects and advantages of the invention will be apparent from the foregoing brief description of the invention and the claims as well as from the detailed description of the drawing in which:

FIG. 1 is a diagrammatic illustration of a chromatographic analyzer system having an absolute back pressure regulator and a pneumatic accumulator.

The invention is described in terms of a typical chromatographic analyzer system where a sample valve is utilized and the output is provided to a recorder. The invention is, however, not limited to this configuration but is applicable to any chromatographic analyzer configuration where a reproducible output is desirable and where a reduction in pressure variations caused by actuation of the chromatographic sample valve is desirable.

Referring now to the drawing, there is shown a chromatographic column 11. A carrier fluid is introduced through conduit means 10 to the carrier gas pressure regulator 9. The carrier gas pressure regulator 9 is preferably a Type 67 manufactured by Fisher Governor Co. From the carrier gas pressure regulator 9 the carrier fluid is introduced through conduit means 12 into sample valve 13. A sample of the fluid to be analyzed is delivered to sample valve 13 through conduit means 14. A conduit means 15 extends between sample valve 13 and the inlet to chromatographic column 11. A conduit means 16 extends between the outlet of chromatographic column 11 and the inlet of the sample detector means 21. Carrier fluid is passed through the reference detector means 22 by being introduced into the inlet of reference detector means 22 through conduit means 18 which communicates with conduit means 12. A flow restriction 19 can be provided in conduit means 18. Carrier fluid also generally flows through sample valve 13 and chromatographic column 11 to the inlet of the sample detection means 21.

At the beginning of an analysis period, sample valve 13 is actuated to introduce a slug of sample of predetermined volume into the carrier fluid flowing through chromatographic column 11. The constituents of the sample slug are eluted in sequence and flow from chromatographic column 11 through conduit means 16 to the sample detector 21.

The sample detector 21 and the reference detector 22 establish a differential output by establishing an electrical signal 31, representative of the composition of the carrier fluid carrying the sample components through the sample detector 21, and an electrical signal 32, representative of the composition of the carrier fluid only in the reference detector 22. Signals 31 and 32 are then compared by detector amplifier 33 to produce signal 34 representative of a chromatographic analyzer output signal. In this preferred embodiment signal 34 is supplied to recording means 35 where it is stored.

The carrier gas pressure regulator 9 is ordinarily referenced by means of a reference pressure vent to atmospheric pressure. In the present invention the carrier gas pressure regulator 9 is referenced to the reference pressure supplied by the absolute back pressure regulator 42 by means of conduit means 41 which is connected to the reference pressure vent of the carrier gas pressure regulator 9. The vent 44 for the sample loop of the chromatographic analyzer sample valve 13 is connected to conduit means 41 through accumulator 45. Thus, the vent 44 is referenced to the reference pressure supplied by the absolute back pressure regulator 42.

The vent 51 from the chromatographic analyzer sample detector 21 and the vent 52 from the chromatographic analyzer reference detector 22 are also connected to conduit means 41. Both vents 51 and 52 are thus referenced to the reference pressure supplied by the absolute back pressure regulator 42. The vent 54 from the absolute back pressure regulator 42 is the only vent to atmosphere or to a disposal container for the chromatographic analyzer system.

In this preferred embodiment of the invention, the absolute back pressure regulator 42 is a Model 43R Absolute Back Pressure regulator manufactured by Moore Products, Philadelphia, Pennsylvania. The operation of such absolute back pressure regulators is well documented and well known. Publication AD43R-1, issue No. 1, Dec. 2, 1959, entitled Model 43R Absolute Back Pressure Regulator by Moore Products, Philadelphia, Pennsylvania provides a complete operational description of the Model 43R Absolute Back Pressure Regulator utilized in the preferred embodiment of the present invention. Essentially, the absolute back pressure regulator 42 acts to maintain a constant reference pressure at the input to the absolute back pressure regulator 42. If the pressure seen at the input to the absolute back pressure regulator 42 should increase then more fluid is vented through conduit means 54 to maintain a constant absolute pressure at the input to the pressure regulator 42. In like manner if the pressure at the input to the absolute back pressure regulator 42 should decrease the amount of fluid vented through conduit means 54 is decreased to again maintain a constant absolute pressure at the input to the absolute back pressure regulator 42. In this manner the pressure seen by the various fluid flows in the chromatographic analyzer system, illustrated in FIG. 1, is a constant. The reference pressure is not affected by changes in barometric pressure or by other system changes. Because of this a very reproducible output over a period of time is obtainable with the chromatographic analyzer system of the present invention.

Flow restriction means 19, which in this preferred embodiment is a needle valve, is provided to adjust the flow of reference fluid to the chromatographic analyzer reference detector 22.

In a particular embodiment of the invention all of the conduit means utilized in the chromatographic analyzer system are 1/16-inch outside diameter (O.D.) stainless steel tubing. The pneumatic accumulator 45 is a piece of ¼-inch O.D. stainless steel tubing having a length of 24 inches. The length and diameter of the pneumatic accumulator 45 may vary as desired. The increased volume of fluid in the pneumatic accumulator 45 acts to smooth out small pressure surges which may result from actuation of the chromatographic analyzer sample valve 13. This prevents the small pressure variations from affecting the referenced pressure and also decreases noise in the chromatographic analyzer system. Thus, the pneumatic accumulator 45 helps to provide a smoother and more reproducible chromatographic analyzer output.

The system of the invention as described above has been applied to a chromatographic analyzer utilized in analyzing the BTU content of gaseous streams. Table I shows the improvement of performance in the system of the present invention over a chromatographic system not employing an absolute back pressure regulator to maintain a constant reference pressure for the chromatographic analyzer system.

TABLE I

| Run | BAROMETRIC PRESSURE mm Hg | CHROMATOGRAPHIC ANALYZER OUTPUT (BTU/ft$^3$) | |
|---|---|---|---|
| | | Pressure Regulated | Pressure Not Regulated |
| 1 | 722 | 1112.4 | |
| 2 | 722 | 1111.8 | |
| 3 | 722 | 1112.6 | |
| 4 | 722 | 1112.1 | |
| 5 | 722 | 1114.6 | |
| 6 | 722 | 1112.3 | |
| 7 | 722 | 1112.6 | |
| 8 | 722 | 1114.4 | |
| 9 | 722 | 1114.5 | |
| 10 | 760 | 1113 | 1078.9 |

TABLE I-continued

| Run | BAROMETRIC PRESSURE mm Hg | CHROMATOGRAPHIC ANALYZER OUTPUT (BTU/ft³) | |
|---|---|---|---|
| | | Pressure Regulated | Pressure Not Regulated |
| 11 | 760 | 1113 | 1081.2 |
| 12 | 760 | 1112.6 | 1080.2 |
| 13 | 760 | 1112.1 | 1082.4 |
| 14 | 760 | 1112.9 | 1081.6 |
| 15 | 760 | 1113.1 | 1078.8 |
| 16 | 760 | 1112 | 1083.6 |
| 17 | 760 | 1112.7 | 1078.9 |
| 18 | 760 | 1112.2 | 1078.8 |
| 19 | 798 | | 1113 |
| 20 | 798 | | 1113 |
| 21 | 798 | | 1112.6 |
| 22 | 798 | | 1112.1 |
| 23 | 798 | | 1112.9 |
| 24 | 798 | | 1113.1 |
| 25 | 798 | | 1112 |
| 26 | 798 | | 1112.7 |
| 27 | 798 | | 1112.2 |

Table I illustrates that when the pressure on the fluid streams in the chromatographic analyzer system is not regulated, the output is a function of changes in atmospheric pressure. The average output of the chromatographic analyzer system was 1080.49 BTU/ft³ at 760 mm Hg. When the pressure changed 38 mm Hg to 798 mm Hg the average output of the chromatographic analyzer system changed to 1112.62 BTU/ft³ for a change of 32.13 BTU/ft³ for a 38 mm Hg change. In contrast the average output of the chromatographic analyzer at a barometric pressure of 722 mm Hg was 1113.03 BTU/ft³ when the pressure seen by the fluid streams in the chromatographic analyzer system was regulated. When the barometric pressure changed 38 mm Hg to 760 mm Hg the average chromatographic analyzer output with the pressure regulator was 1112.62 BTU/ft³ or a change of 0.41 BTU/ft³ for a change of 38 mm Hg in barometric pressure. This change is within the noise level of the chromatographic analyzer system and is not statistically significant.

As is illustrated in Table I the chromatographic analyzer output where pressure regulation is employed would be reproducible over a period of time even though changes in barometric pressure occurred.

Table I also illustrates that the chromatographic analyzer output in a chromatographic analyzer system where the pressure seen by fluid streams is not regulated but is allowed to vary as a function of barometric pressure is not reproducible over a period of time if changes in barometric pressure occur. In a process such as a BTU analysis, where the price of a product is determined by the BTU analysis, changes in barometric pressure may result in serious financial losses if the pressure is not regulated.

The invention has been described in terms of its presently preferred embodiment as is illustrated in FIG. 1. A suitable sample valve 13 is illustrated and described in U.S. Pat. No. 3,545,491. While the invention has been described in terms of the presently preferred embodiment reasonable variations and modifications are possible by those skilled in the art, within the scope of the described invention and the appended claims.

That which is claimed is:

1. In the method of chromatographically analyzing a fluid stream which comprises passing a carrier fluid through a chromatographic separating column, using a sample valve means to intermittently pass a sample of said fluid stream through said chromatographic separating column and then passing the effluent of said chromatographic separating column through a detector means to identify the components of said effluent, said sample valve means having a sample outlet means for withdrawing said fluid stream, said detector means providing a chromatographic analyzer output which varies in accordance with the composition of said sample of said fluid stream, the improvement of providing a reproducible chromatographic analyzer output over a period of time comprising the steps of:

referencing the fluid streams passing through said sample outlet means and said detector means to a constant reference pressure to thereby reduce changes in said chromatographic analyzer output caused by changes in barometric pressure; and utilizing a pneumatic accumulator in said sample outlet means to thereby reduce pressure fluctuations caused by actuation of said sample valve means, thus providing a smoother and more reproducible chromatographic analyzer output.

2. Apparatus comprising:

a chromatographic separating column having a fluid inlet and a fluid outlet;

a sample valve means having a sample inlet, a carrier fluid inlet, a fluid outlet and a sample outlet means;

means for passing carrier fluid from the fluid outlet of said sample valve means to the fluid inlet of said chromatographic separating column, said sample valve means being adapted to interrupt the flow of said carrier fluid to inject a slug of sample into said carrier fluid passing to said chromatographic separating column;

a pressure regulator means having a fluid inlet, a fluid outlet and a reference pressure vent;

means for supplying a carrier fluid to said fluid inlet of said pressure regulator means;

means for supplying said carrier fluid from the fluid outlet of said pressure regulator means to said carrier fluid inlet of said sample valve means;

means for supplying a sample fluid to said sample inlet of said sample valve means, said sample outlet means being utilized to withdraw at least a portion of said sample fluid from said sample valve means;

a sample detector means having a fluid inlet and a fluid outlet;

means for supplying the effluent from the fluid outlet of said chromatographic separating column to the fluid inlet of said sample detector means;

a reference detector means having a fluid inlet and a fluid outlet;

means for supplying said carrier fluid from the fluid outlet of said pressure regulator means to the fluid inlet of said reference detector means;

an absolute back pressure regulator means having a fluid inlet and a fluid outlet, said absolute back pressure regulator means being adapted to maintain a constant reference pressure at the fluid inlet of said absolute back pressure regulator means;

a pneumatic accumulator means having a fluid inlet and a fluid outlet, the fluid flowing through said sample outlet means of said sample valve means being provided to the fluid inlet of said pneumatic accumulator means;

means for supplying the fluid flowing from the fluid outlet of said pneumatic accumulator means to the fluid inlet of said absolute back pressure regulator means;

means for supplying the fluid flowing from the fluid outlet of said sample detector means to the fluid inlet of said absolute back pressure regulator means;

means for supplying the fluid flowing from the fluid outlet of said reference detector means to the fluid inlet of said absolute back pressure regulator means; and means for connecting said reference pressure vent of said pressure regulator means to the fluid inlet of said absolute back pressure regulator means.

3. Apparatus in accordance with claim 2 wherein said pneumatic accumulator means is a conduit means having a larger diameter than said sample outlet means of said sample valve means.

4. Apparatus in accordance with claim 3 wherein said pneumatic accumulator means is a conduit means having a ¼ inch outside diameter and a length of 24 inches and said sample outlet means of said sample valve means is a conduit means having a 1/16 inch outside diameter.

* * * * *